(12) United States Patent
Dachs, II et al.

(10) Patent No.: US 11,446,105 B2
(45) Date of Patent: *Sep. 20, 2022

(54) SIGNAL CONNECTOR FOR STERILE BARRIER BETWEEN SURGICAL INSTRUMENT AND TELEOPERATED ACTUATOR

(71) Applicant: Intuitive Surgical Operations, Inc., Sunnyvale, CA (US)

(72) Inventors: Gregory W. Dachs, II, San Mateo, CA (US); Tyler J. Morrissette, Old Lyme, CT (US); Bruce Michael Schena, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 517 days.

This patent is subject to a terminal disclaimer.

(21) Appl. No.: 16/524,832

(22) Filed: Jul. 29, 2019

(65) Prior Publication Data

US 2019/0380803 A1    Dec. 19, 2019

Related U.S. Application Data

(63) Continuation of application No. 15/121,731, filed as application No. PCT/US2015/020888 on Mar. 17, 2015, now Pat. No. 10,363,109.

(Continued)

(51) Int. Cl.
*A61B 46/10* (2016.01)
*A61B 46/00* (2016.01)
(Continued)

(52) U.S. Cl.
CPC ........ *A61B 46/10* (2016.02); *A61B 17/00234* (2013.01); *A61B 34/30* (2016.02);
(Continued)

(58) Field of Classification Search
CPC ......... A61B 46/10; A61B 34/30; A61B 34/35; A61B 34/37; A61B 46/40; A61B 90/08;
(Continued)

(56) References Cited

U.S. PATENT DOCUMENTS

| 4,542,272 A | 9/1985 | Hubbard et al. |
| 5,069,221 A | 12/1991 | Smith et al. |

(Continued)

FOREIGN PATENT DOCUMENTS

| CN | 1631622 A | 6/2005 |
| CN | 101297267 A | 10/2008 |

(Continued)

OTHER PUBLICATIONS

Extended European Search Report for Application No. EP20159147.6, dated Jun. 16, 2020, 7 pages.

(Continued)

*Primary Examiner* — Ophelia A Hawthorne
(74) *Attorney, Agent, or Firm* — Jones Robb, PLLC

(57) ABSTRACT

An instrument sterile drape includes a plastic sheet and an instrument sterile adapter (ISA) coupled to the plastic sheet. The ISA includes bottom and top plates located on opposite sides of the plastic sheet plate and joined together. A passage in the bottom plate allows an instrument carriage flux connection to pass through the plastic sheet and the bottom plate to be adjacent to the top plate. The top plate includes a signal transmission area that will be adjacent to an upper surface of the flux connection of the instrument carriage. A flux connector may close an opening in the signal transmission area of the top plate and provide a path for an electrical or optical signal. The signal transmission area of the top plate may be thinned to allow an RFID sensor to be closer to an RFID device in a surgical instrument attached to the instrument sterile adapter.

20 Claims, 8 Drawing Sheets

Related U.S. Application Data

(60) Provisional application No. 62/104,306, filed on Jan. 16, 2015, provisional application No. 62/103,991, filed on Jan. 15, 2015, provisional application No. 62/019,318, filed on Jun. 30, 2014, provisional application No. 61/954,595, filed on Mar. 17, 2014, provisional application No. 61/954,571, filed on Mar. 17, 2014, provisional application No. 61/954,557, filed on Mar. 17, 2014, provisional application No. 61/954,502, filed on Mar. 17, 2014, provisional application No. 61/954,497, filed on Mar. 17, 2014.

(51) Int. Cl.

| | | |
|---|---|---|
| *A61B 34/30* | (2016.01) | |
| *A61B 34/37* | (2016.01) | |
| *A61B 90/00* | (2016.01) | |
| *A61B 34/35* | (2016.01) | |
| *A61B 90/98* | (2016.01) | |
| *A61B 17/00* | (2006.01) | |
| *A61B 46/23* | (2016.01) | |
| *F16H 1/20* | (2006.01) | |

(52) U.S. Cl.
CPC .............. *A61B 34/35* (2016.02); *A61B 34/37* (2016.02); *A61B 46/40* (2016.02); *A61B 90/08* (2016.02); *A61B 90/361* (2016.02); *A61B 90/98* (2016.02); *A61B 46/23* (2016.02); *A61B 2017/00477* (2013.01); *A61B 2090/0813* (2016.02); *F16H 1/20* (2013.01); *Y10T 29/49817* (2015.01); *Y10T 403/59* (2015.01)

(58) Field of Classification Search
CPC . A61B 90/361; A61B 90/98; A61B 17/00234; A61B 46/00; A61B 2046/205
See application file for complete search history.

(56) References Cited

U.S. PATENT DOCUMENTS

| | | |
|---|---|---|
| 5,214,573 A | 5/1993 | Roza, I |
| 5,679,423 A | 10/1997 | Shah |
| 5,803,086 A | 9/1998 | Scholz et al. |
| 6,331,181 B1 | 12/2001 | Tierney et al. |
| 6,471,172 B1 | 10/2002 | Lemke et al. |
| 7,096,870 B2 | 8/2006 | Lamprich et al. |
| 7,125,403 B2 | 10/2006 | Julian et al. |
| 7,758,569 B2 | 7/2010 | Brock |
| 7,947,050 B2 | 5/2011 | Lee et al. |
| 7,963,913 B2 | 6/2011 | Devengenzo et al. |
| 8,220,468 B2 | 7/2012 | Cooper et al. |
| 8,506,555 B2 | 8/2013 | Ruiz et al. |
| 8,529,582 B2 | 9/2013 | Devengenzo et al. |
| 8,555,892 B2 | 10/2013 | Traub |
| 8,998,930 B2 | 4/2015 | Orban, III |
| 9,687,312 B2 | 6/2017 | Dachs, II et al. |
| 9,839,487 B2 | 12/2017 | Dachs, II et al. |
| 10,022,193 B2 | 7/2018 | Cooper et al. |
| 10,045,828 B2 | 8/2018 | Dachs, II et al. |
| 10,213,268 B2 | 2/2019 | Dachs, II et al. |
| 10,278,784 B2 | 5/2019 | Dachs, II |
| 10,363,109 B2 * | 7/2019 | Dachs, II .............. A61B 46/40 |
| 10,420,622 B2 | 9/2019 | Dachs et al. |
| 10,485,621 B2 | 11/2019 | Morrissette et al. |
| 10,537,400 B2 | 1/2020 | Dachs, II et al. |
| 10,543,051 B2 | 1/2020 | Schena et al. |
| 10,595,836 B2 | 3/2020 | Smaby et al. |
| 10,610,320 B2 | 4/2020 | Dachs, II et al. |
| 10,639,119 B2 | 5/2020 | Dachs, II et al. |
| 10,898,288 B2 | 1/2021 | Dachs, II et al. |
| 10,912,616 B2 | 2/2021 | Dachs, II et al. |
| 11,045,274 B2 | 6/2021 | Dachs, II et al. |
| 2002/0032452 A1 | 3/2002 | Tierney et al. |
| 2002/0111635 A1 | 8/2002 | Jensen et al. |
| 2002/0143319 A1 | 10/2002 | Brock |
| 2003/0216723 A1 | 11/2003 | Shinmura et al. |
| 2004/0049205 A1 | 3/2004 | Lee et al. |
| 2005/0119527 A1 | 6/2005 | Banik et al. |
| 2005/0240178 A1 | 10/2005 | Morley et al. |
| 2005/0244217 A1 | 11/2005 | Burke et al. |
| 2006/0235436 A1 | 10/2006 | Anderson et al. |
| 2006/0260622 A1 | 11/2006 | Wooley et al. |
| 2006/0273135 A1 | 12/2006 | Beetel |
| 2007/0012135 A1 | 1/2007 | Tierney et al. |
| 2007/0142971 A1 | 6/2007 | Schena et al. |
| 2008/0103491 A1 | 5/2008 | Omori et al. |
| 2008/0140088 A1 | 6/2008 | Orban, III |
| 2009/0248038 A1 | 10/2009 | Blumenkranz et al. |
| 2010/0152566 A1 | 6/2010 | Rains et al. |
| 2010/0163057 A1 | 7/2010 | Anderson et al. |
| 2010/0170519 A1 | 7/2010 | Romo et al. |
| 2010/0175701 A1 | 7/2010 | Reis et al. |
| 2010/0234857 A1 | 9/2010 | Itkowitz et al. |
| 2011/0015650 A1 | 1/2011 | Choi et al. |
| 2011/0084113 A1 | 4/2011 | Bedi et al. |
| 2011/0118754 A1 | 5/2011 | Dachs, II et al. |
| 2011/0213383 A1 | 9/2011 | Lee et al. |
| 2011/0277776 A1 | 11/2011 | McGrogan et al. |
| 2011/0288560 A1 | 11/2011 | Shohat et al. |
| 2011/0290854 A1 | 12/2011 | Timm et al. |
| 2011/0290855 A1 | 12/2011 | Moore et al. |
| 2011/0295270 A1 | 12/2011 | Giordano et al. |
| 2011/0313477 A1 | 12/2011 | McLean et al. |
| 2012/0197094 A1 | 8/2012 | Zhang et al. |
| 2012/0239060 A1 | 9/2012 | Orban, III et al. |
| 2012/0247489 A1 | 10/2012 | Orban, III et al. |
| 2012/0292367 A1 | 11/2012 | Morgan et al. |
| 2013/0110129 A1 | 5/2013 | Reid et al. |
| 2013/0211397 A1 | 8/2013 | Parihar et al. |
| 2013/0211401 A1 | 8/2013 | Bailey et al. |
| 2013/0274062 A1 | 10/2013 | Arai et al. |
| 2013/0274657 A1 | 10/2013 | Zirps et al. |
| 2013/0325034 A1 | 12/2013 | Schena et al. |
| 2013/0331858 A1 | 12/2013 | Devengenzo et al. |
| 2014/0001234 A1 | 1/2014 | Shelton, IV et al. |
| 2014/0066944 A1 | 3/2014 | Taylor et al. |
| 2014/0069437 A1 | 3/2014 | Reis et al. |
| 2015/0223832 A1 | 8/2015 | Swaney et al. |
| 2015/0257841 A1 | 9/2015 | Dachs, II et al. |
| 2016/0184037 A1 | 6/2016 | Cooper et al. |
| 2016/0354173 A1 | 12/2016 | Dachs, II et al. |
| 2016/0361049 A1 | 12/2016 | Dachs, II et al. |
| 2016/0361124 A1 | 12/2016 | Dachs, II et al. |
| 2016/0361126 A1 | 12/2016 | Schena et al. |
| 2016/0361129 A1 | 12/2016 | Morrissette et al. |
| 2016/0361131 A1 | 12/2016 | Dachs, II et al. |
| 2016/0367328 A1 | 12/2016 | Dachs, II et al. |
| 2017/0172549 A1 | 6/2017 | Smaby et al. |
| 2018/0064501 A1 | 3/2018 | Dachs, II |
| 2018/0168752 A1 | 6/2018 | Scheib et al. |
| 2018/0344419 A1 | 12/2018 | Dachs, II et al. |
| 2019/0183596 A1 | 6/2019 | Dachs, II |
| 2019/0254766 A1 | 8/2019 | Dachs, II |
| 2019/0365494 A1 | 12/2019 | Dachs, II et al. |
| 2020/0069389 A1 | 3/2020 | Morrissette et al. |
| 2020/0155130 A1 | 5/2020 | Smaby et al. |
| 2020/0222139 A1 | 7/2020 | Dachs, II et al. |
| 2020/0229886 A1 | 7/2020 | Dachs, II et al. |
| 2020/0281677 A1 | 9/2020 | Dachs, II et al. |
| 2021/0137627 A1 | 5/2021 | Dachs, II et al. |
| 2021/0196420 A1 | 7/2021 | Dachs, II et al. |

FOREIGN PATENT DOCUMENTS

| | | |
|---|---|---|
| CN | 101443162 A | 5/2009 |
| CN | 102630154 A | 8/2012 |
| CN | 203234838 U | 10/2013 |
| DE | 20015892 U1 | 1/2001 |
| DE | 102012008535 A1 | 10/2013 |
| DE | 102012013242 A1 | 1/2014 |
| EP | 1862123 A2 | 12/2007 |
| EP | 2259744 A1 | 12/2010 |

(56) References Cited

FOREIGN PATENT DOCUMENTS

| | | | |
|---|---|---|---|
| GB | 2538326 | A | 11/2016 |
| JP | H0666326 | A | 3/1994 |
| JP | H07163574 | A | 6/1995 |
| JP | 2001187067 | A | 7/2001 |
| JP | 2012050706 | A | 3/2012 |
| JP | 2012210294 | A | 11/2012 |
| JP | 2013034859 | A | 2/2013 |
| KR | 20080100212 | A | 11/2008 |
| KR | 20110032444 | A | 3/2011 |
| KR | 20110036452 | A | 4/2011 |
| KR | 20110095795 | A | 8/2011 |
| KR | 20130080638 | A | 7/2013 |
| KR | 20130120316 | A | 11/2013 |
| WO | WO-2007075864 | A1 | 7/2007 |
| WO | WO-2007095637 | A1 | 8/2007 |
| WO | WO-2007126443 | A2 | 11/2007 |
| WO | WO-2007142698 | A2 | 12/2007 |
| WO | WO-2008101228 | A2 | 8/2008 |
| WO | WO-2009123925 | A1 | 10/2009 |
| WO | WO-2009151205 | A1 | 12/2009 |
| WO | WO-2010126128 | A1 | 11/2010 |
| WO | WO-2011037394 | A2 | 3/2011 |
| WO | WO-2011143016 | A1 | 11/2011 |
| WO | WO-2012158449 | A1 | 11/2012 |
| WO | WO-2013018931 | A1 | 2/2013 |
| WO | WO-2013181536 | A1 | 12/2013 |
| WO | WO-2014005689 | A2 | 1/2014 |
| WO | WO-2014035803 | A1 | 3/2014 |
| WO | WO-2015023730 | A1 | 2/2015 |
| WO | WO-2015142824 | A1 | 9/2015 |

OTHER PUBLICATIONS

Extended European Search Report for Application No. EP19201778.8, dated Nov. 27, 2019, 5 pages.
Extended European Search Report for Application No. EP20154204.0, dated May 7, 2020, 7 pages.
Extended European Search Report for Application No. EP20154737.9, dated Apr. 17, 2020, 10 pages.
Extended European Search Report for Application No. EP20161337.9, dated May 7, 2020, 8 pages.
Extended European Search Report for Application No. 19181058.9 dated Aug. 22, 2019. 7 pages.
Extended European Search Report for Application No. 15766019.2, dated Oct. 20, 2017, 7 pages.
Extended European Search Report for Application No. EP15764610.0, dated Nov. 23, 2017, 8 pages.
International Search Report and Written Opinion for Application No. PCT/US15/20876, dated Jun. 12, 2015, 17 pages.
International Search Report and Written Opinion for Application No. PCT/US15/20880, dated Jul. 14, 2015, 9 pages.
International Search Report and Written Opinion for Application No. PCT/US15/20882, dated May 29, 2015, 14 pages.
International Search Report and Written Opinion for Application No. PCT/US15/20884, dated Jun. 12, 2015, 13 pages.
International Search Report and Written Opinion for Application No. PCT/US15/20885, dated Jun. 5, 2015, 7 pages.
International Search Report and Written Opinion for Application No. PCT/US15/20886, dated Jun. 4, 2015, 19 pages.
International Search Report and Written Opinion for Application No. PCT/US15/20888, dated Jun. 5, 2015, 9 pages.
International Search Report and Written Opinion for Application No. PCT/US15/21020, dated Jun. 5, 2015, 10 pages.
International Search Report and Written Opinion for Application No. PCT/US15/21111, dated May 21, 2015, 10 pages.
Extended European Search Report for Application No. 15765493.0, dated Jul. 28, 2017, 7 pages.
Extended European Search Report for Application No. EP15764089.7, dated Oct. 25, 2017, 11 pages.
Extended European Search Report for Application No. EP15764268.7, dated Nov. 6, 2017, 8 pages.
Extended European Search Report for Application No. EP15764881.7, dated Nov. 30, 2017, 10 pages.
Extended European Search Report for Application No. EP15764940.1, dated Oct. 30, 2017, 8 pages.
Extended European Search Report for Application No. 15765779.2, dated Jul. 18, 2017, 8 pages.
Extended European Search Report for Application No. EP15764745.4, dated Oct. 30, 2017, 10 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP20172196.6 dated Aug. 7, 2020, 8 pages.

* cited by examiner

SIGNAL CONNECTOR FOR STERILE BARRIER BETWEEN SURGICAL INSTRUMENT AND TELEOPERATED ACTUATOR

This application is a continuation of application Ser. No. 15/121,731, filed 25 Aug. 2016 (25-08-2016), which is a national stage application filed under 35 U.S.C. § 371 of PCT/US2015/020888, filed 17 Mar. 2015 (17-03-2015), which claims the benefit of and priority to
U.S. Provisional Application No. 61/954,497, filed 17 Mar. 2014 (17-03-2014),
U.S. Provisional Application No. 61/954,502, filed 17 Mar. 2014 (17-03-2014),
U.S. Provisional Application No. 61/954,557, filed 17 Mar. 2014 (17-03-2014),
U.S. Provisional Application No. 61/954,571, filed 17 Mar. 2014 (17-03-2014),
U.S. Provisional Application No. 61/954,595, filed 17 Mar. 2014 (17-03-2014),
U.S. Provisional Application No. 62/019,318, filed 30 Jun. 2014 (30-06-2014),
U.S. Provisional Application No. 62/103,991, filed 15 Jan. 2015 (15-01-2015), and
U.S. Provisional Application No. 62/104,306, filed 16 Jan. 2015 (16-01-2015). Each of these applications is specifically incorporated herein by reference to the greatest extent permitted.

FIELD

Embodiments of the invention relate to the field of field of signal connectors; and more specifically, to signal connectors for surgical drapes placed between teleoperated actuators and surgical instruments.

BACKGROUND

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas, and cannula sleeves are passed through small (approximately 12 mm) incisions in the musculature of the patient's abdomen to provide entry ports through which laparoscopic surgical instruments can be passed in a sealed fashion.

The laparoscopic surgical instruments generally include a laparoscope for viewing the surgical field and surgical instruments having end effectors. Typical surgical end effectors include clamps, graspers, scissors, staplers, and needle holders, for example. The surgical instruments are similar to those used in conventional (open) surgery, except that the working end or end effector of each surgical instrument is separated from its handle by an approximately 30 cm. long extension tube, for example, so as to permit the operator to introduce the end effector to the surgical site and to control movement of the end effector relative to the surgical site from outside a patient's body.

In order to provide improved control of the end effector, it may be desirable to control the surgical instrument with teleoperated actuators. The surgeon may operate controls on a console to indirectly manipulate the instrument that is connected to the teleoperated actuators. The surgical instrument is detachably coupled to the teleoperated actuators so that the surgical instrument can be separately sterilized and selected for use as needed instrument for the surgical procedure to be performed. The surgical instrument may be changed during the course of a surgery.

Performing surgery with teleoperated surgical instruments creates new challenges. One challenge is the need to maintain the region adjacent the patient in a sterile condition. However, the motors, sensors, encoders and electrical connections that are necessary to control the surgical instruments typically cannot be sterilized using conventional methods, e.g., steam, heat and pressure or chemicals, because they would be damaged or destroyed in the sterilization process.

Another challenge with teleoperated surgery systems is that a number of connections are required between the surgical instrument and the teleoperated actuator and its controller. Connections are required to transmit the actuator forces, electrical signals, and data. This makes the attachment of the surgical instrument to the teleoperated actuator and its controller complex.

Still another challenge with servo actuated teleoperated surgery systems is that an operating room is not an ideal environment for preparing precision mechanical assemblies.

It is desirable to provide an effective sterile barrier interface between a surgical system's teleoperated actuator and a surgical instrument controlled by the actuator. Although known sterile barrier interfaces have been effective, the need to improve work flow for patient-side surgical personnel and to accommodate advances in teleoperated surgical instrument designs and capabilities requires improved sterile interfaces. Among the required improvements are an ability to quickly, easily, and reliably mount the sterile barrier interface (with its associated sterile barrier drape) to the actuator's mechanical drive elements and to the surgical system's information communication interface points; an ability to quickly, easily, and reliably mount a surgical instrument to the interface so that the actuator's mechanical drive functions and the system's information communication functions are effectively coupled to the surgical instrument; an ability to quickly, easily disengage and dismount the surgical instrument from the interface so that another surgical instrument can be mounted and engaged in its place; and an ability to quickly and easily disengage and dismount the interface from the actuator. In addition, such improved interfaces must be mechanically rugged and both easy and inexpensive to manufacture.

SUMMARY

An instrument sterile drape includes a plastic sheet and an instrument sterile adapter (ISA) coupled to the plastic sheet. The ISA includes bottom and top plates located on opposite sides of the plastic sheet plate and joined together. A passage in the bottom plate allows an instrument carriage flux connection to pass through the plastic sheet and the bottom plate to be adjacent to the top plate. The top plate includes a signal transmission area that will be adjacent to an upper surface of the flux connection of the instrument carriage. A flux connector may close an opening in the signal transmission area of the top plate and provide a path for an electrical or optical signal. The signal transmission area of the top plate may be thinned to allow an RFID sensor to be closer to an RFID device in a surgical instrument attached to the instrument sterile adapter.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 4 is a perspective view of a strut portion of the setup joint shown in

FIG. 3.

DESCRIPTION OF EMBODIMENTS

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
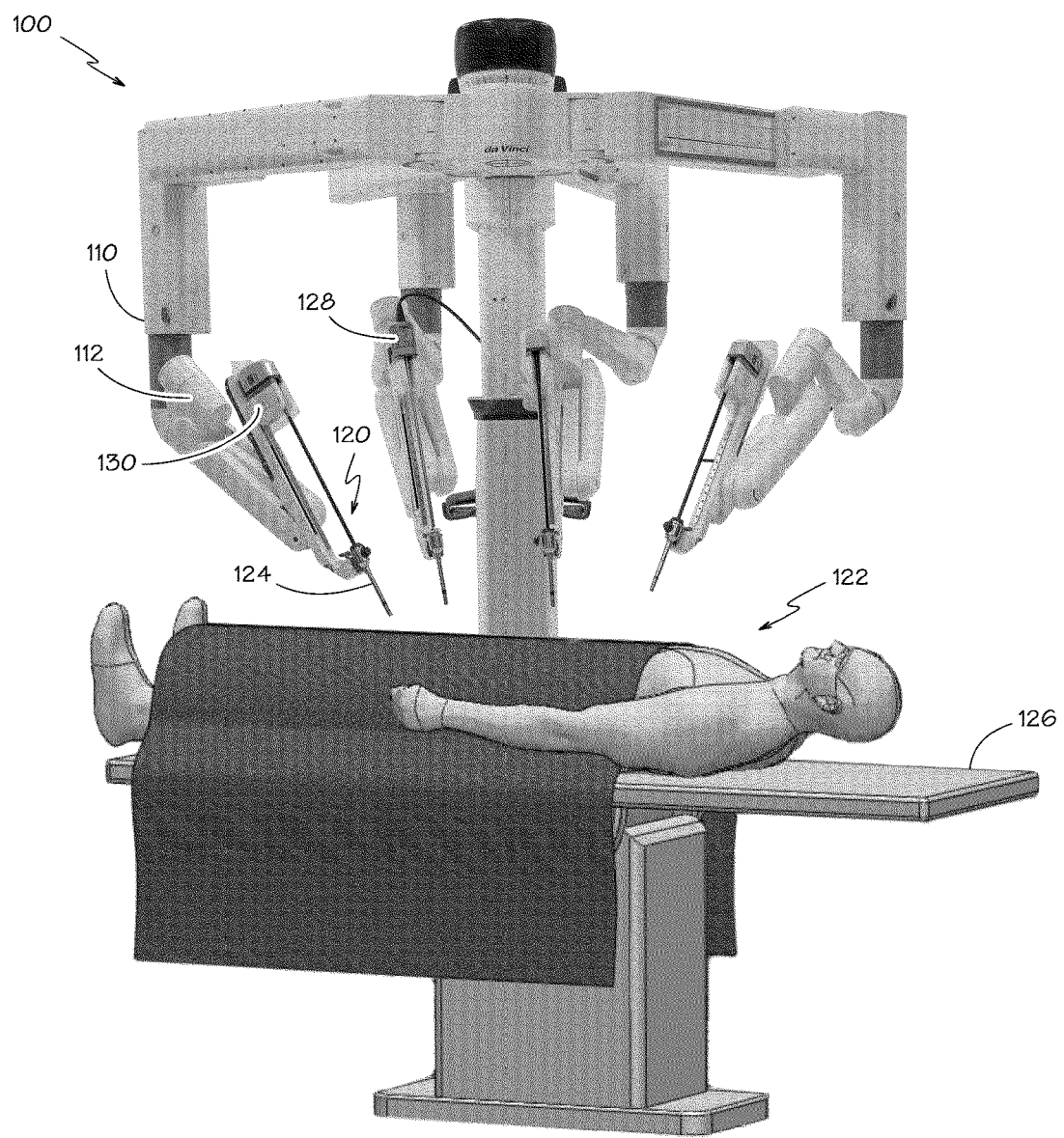
FIG. 1 is a view of an illustrative patient-side portion 100 of a teleoperated surgical system.

FIG. 1 is a view of an illustrative patient-side portion 100 of a teleoperated surgical system, in accordance with embodiments of the present invention. The patient-side portion 100 includes support assemblies 110 and one or more surgical instrument manipulators 112 at the end of each support assembly. The support assemblies optionally include one or more unpowered, lockable setup joints that are used to position the surgical instrument manipulator(s) 112 with reference to the patient for surgery. As depicted, the patient-side portion 100 rests on the floor. In other embodiments the patient-side portion may be mounted to a wall, to the ceiling, to the operating table 126, which also supports the patient's body 122, or to other operating room equipment. Further, while the patient-side portion 100 is shown as including four manipulators 112, more or fewer manipulators 112 may be used. Still further, the patient-side portion 100 may consist of a single assembly as shown, or it may include two or more separate assemblies, each optionally mounted in various possible ways.

Each surgical instrument manipulator 112 supports one or more surgical instruments 120 that operate at a surgical site within the patient's body 122. Each manipulator 112 may be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 112 to move its associated surgical instrument around a center of motion on the instrument that stays stationary with reference to the patient, and this center of motion is typically located to be at the position where the instrument enters the body.

The term "surgical instrument" is used herein to describe a medical device configured to be inserted into a patient's body and used to carry out surgical or diagnostic procedures. The surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some surgical instruments used with embodiments of the invention further provide an articulated support (sometimes referred to as a "wrist") for the end effector so that the position and orientation of the end effector can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

A functional teleoperated surgical system will generally include a vision system portion (not shown) that enables the operator to view the surgical site from outside the patient's body 122. The vision system typically includes a surgical instrument that has a video-image-capture function 128 (a "camera instrument") and one or more video displays for displaying the captured images. In some surgical system configurations, the camera instrument 128 includes optics that transfer the images from the distal end of the camera instrument 128 to one or more imaging sensors (e.g., CCD or CMOS sensors) outside of the patient's body 122. Alternatively, the imaging sensor(s) may be positioned at the distal end of the camera instrument 128, and the signals produced by the sensor(s) may be transmitted along a lead or wirelessly for processing and display on the video display. An illustrative video display is the stereoscopic display on the surgeon's console in surgical systems commercialized by Intuitive Surgical, Inc., Sunnyvale, Calif.

A functional teleoperated surgical system will further include a control system portion (not shown) for controlling the movement of the surgical instruments 120 while the instruments are inside the patient. The control system portion may be at a single location in the surgical system, or it may be distributed at two or more locations in the system (e.g., control system portion components may be in the system's patient-side portion 100, in a dedicated system control console, or in a separate equipment rack). The teleoperated master/slave control may be done in a variety of ways, depending on the degree of control desired, the size of the surgical assembly being controlled, and other factors. In some embodiments, the control system portion includes one or more manually-operated input devices, such as a joystick, exoskeletal glove, a powered and gravity-compensated manipulator, or the like. These input devices control teleoperated motors which, in turn, control the movement of the surgical instrument.

The forces generated by the teleoperated motors are transferred via drivetrain mechanisms, which transmit the forces from the teleoperated motors to the surgical instrument 120. In some telesurgical embodiments, the input devices that control the manipulator(s) may be provided at a location remote from the patient, either inside or outside the room in which the patient is placed. The input signals from the input devices are then transmitted to the control system portion. Persons familiar with telemanipulative, teleoperative, and telepresence surgery will know of such systems and their components, such as the da Vinci® Surgical System commercialized by Intuitive Surgical, Inc. and the Zeus® Surgical System originally manufactured by Computer Motion, Inc., and various illustrative components of such systems.

As shown, both the surgical instrument 120 and an optional entry guide 124 (e.g., a cannula in the patient's abdomen) are removably coupled to the distal end of a manipulator 112, with the surgical instrument 120 inserted through the entry guide 124. Teleoperated actuators in the manipulator 112 move the surgical instrument 120 as a whole. The manipulator 112 further includes an instrument carriage 130. The surgical instrument 120 is detachably connected to the carriage 130. The teleoperated actuators housed in the carriage 130 provide a number of controller motions which the surgical instrument 120 translates into a variety of movements of the end effector on the surgical instrument. Thus the teleoperated actuators in the carriage 130 move only one or more components of the surgical instrument 120 rather than the instrument as a whole. Inputs to control either the instrument as a whole or the instrument's components are such that the input provided by a surgeon to the control system portion (a "master" command) is translated into a corresponding action by the surgical instrument (a "slave" response).

Figure 2:
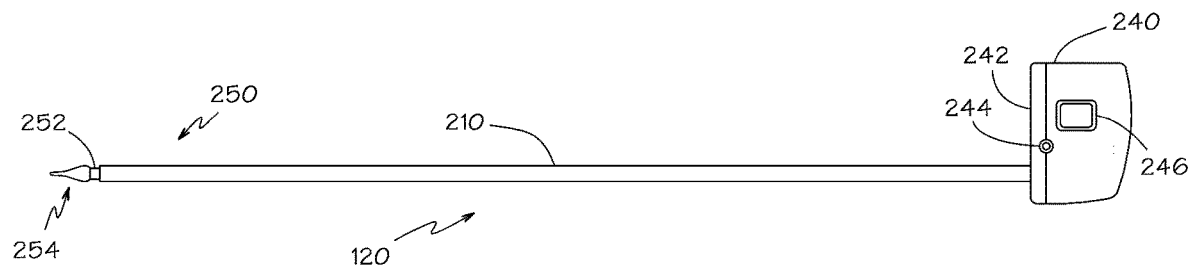
FIG. 2 is a side view of a surgical instrument for use with a teleoperated actuator.

FIG. 2 is a side view of an illustrative embodiment of the surgical instrument 120, comprising a distal portion 250 and a proximal control mechanism 240 coupled by an elongate tube 210. The distal portion 250 of the surgical instrument 120 may provide any of a variety of end effectors such as the forceps 254 shown, a needle driver, a cautery device, a cutting tool, an imaging device (e.g., an endoscope or ultrasound probe), or a combined device that includes a combination of two or more various tools and imaging devices. In the embodiment shown, the end effector 254 is coupled to the elongate tube 210 by a "wrist" 252 that allows the orientation of the end effector to be manipulated with reference to the instrument tube 210.

Figure 3:
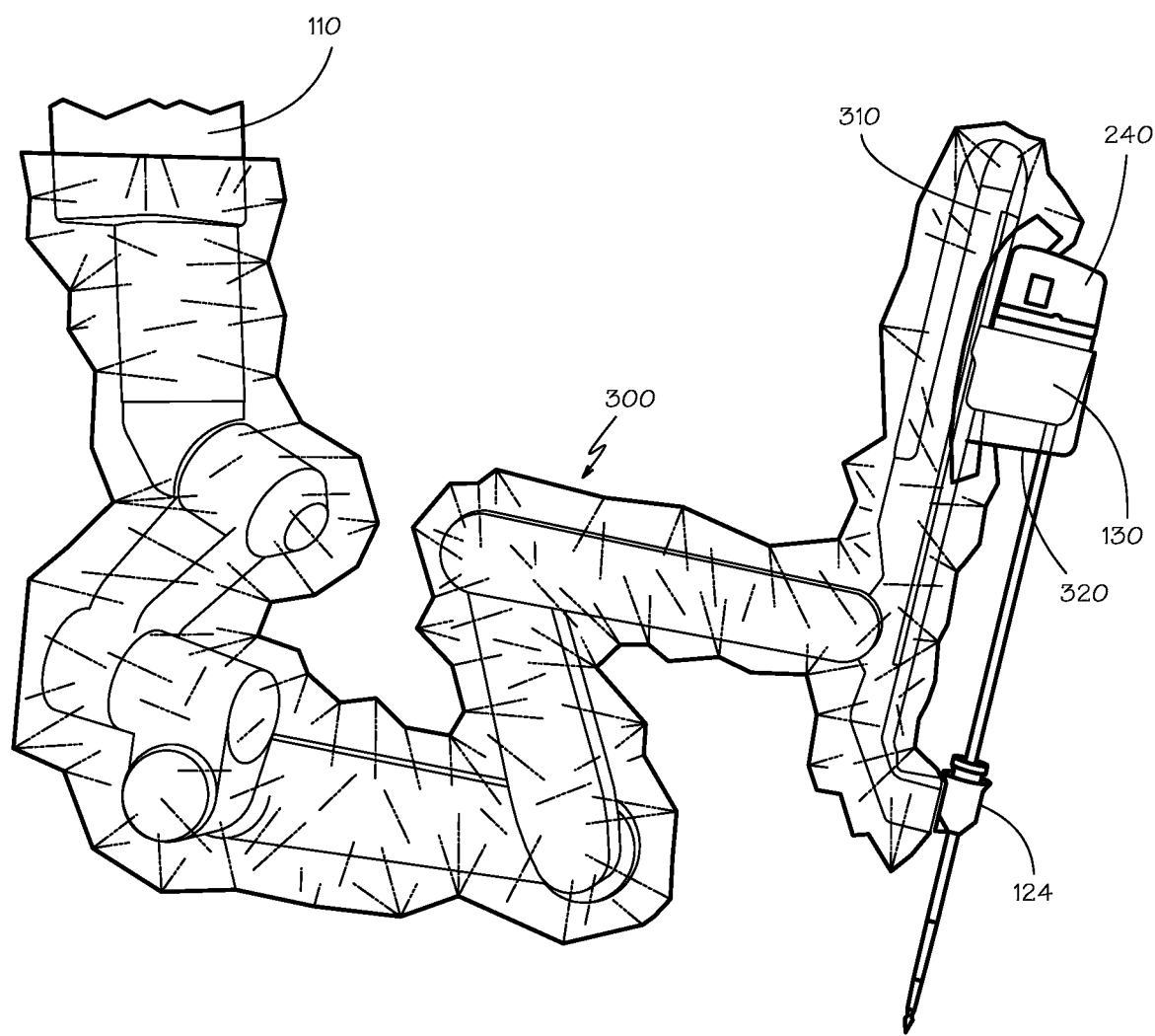
FIG. 3 is a perspective view of a setup joint.

FIG. 3 is a perspective view of an arm that extends from a setup joint 110. The arm supports the carriage 130 which in turn supports the surgical instrument 120 on a strut 310. In preparation for surgery, the setup joint is covered with a sterile drape 300. The sterile drape protects the arm from contamination and provides a sterile surface around the arm. The majority of the sterile drape 300 is a plastic sheet, which may be in the form of a tube or bag, that covers the arm. For example, a single layer thermoplastic polyurethane (TPU) or other suitable material may be used for the plastic sheet. A lubricant may be compounded in to reduce the tackiness of the plastic. The sheet may be about 100 micrometers (0.004 inch) thick.

Figure 4:
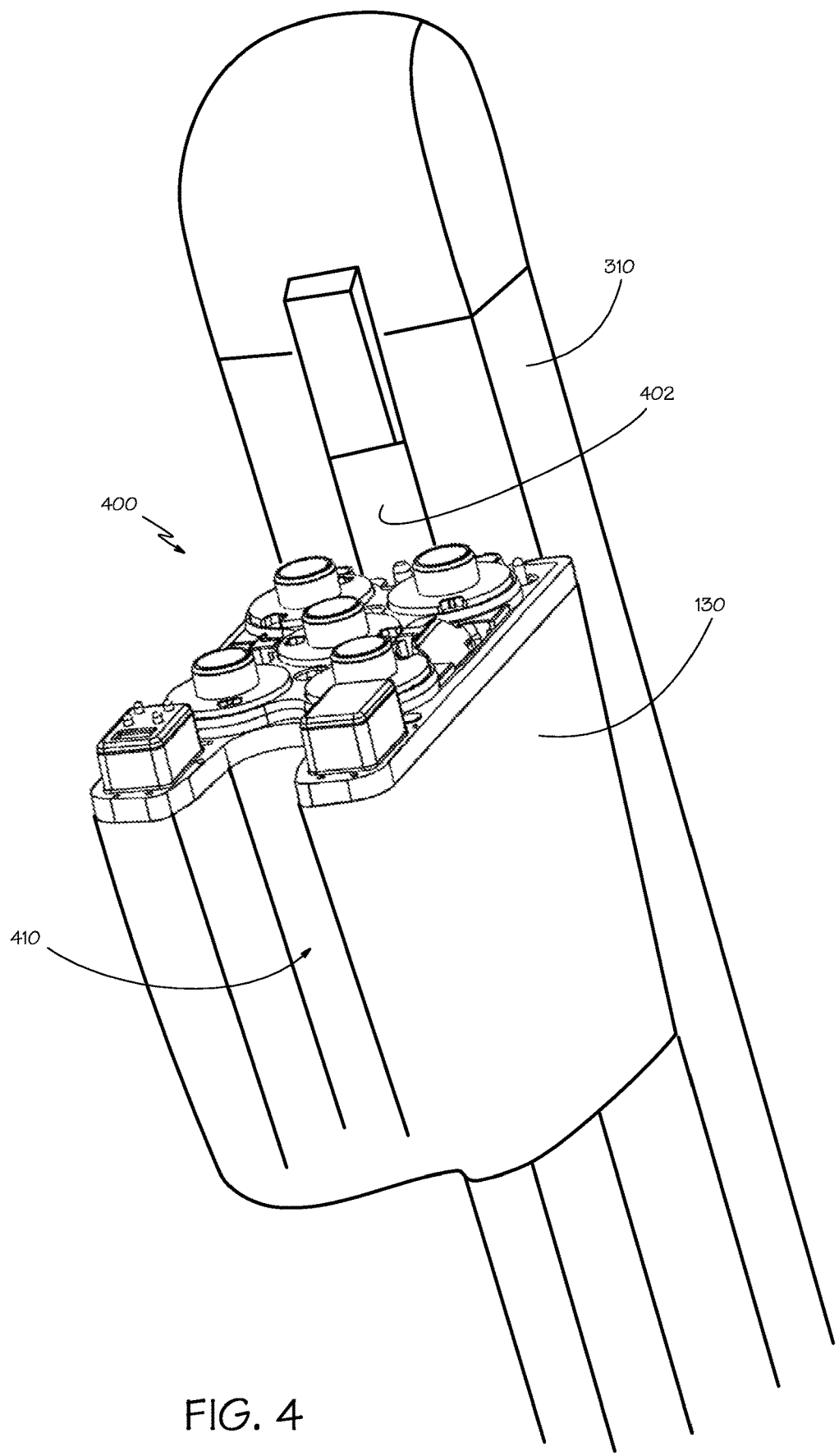

FIG. 4 is a perspective view of the strut 310 portion of the arm that supports the carriage 130. A spar 402 positions the carriage 130 on the strut 310. The sterile drape is not shown to allow the carriage 130 to be seen more clearly. A surface 400 of the carriage provides a number of mechanical and electrical interfaces to communicate mechanical motion and data signals between the control system, the actuators, and the surgical instrument. It will be appreciated that the connections to the surgical instrument may require a penetration through the sterile drape. It is difficult to provide a penetration through the plastic sheet that is compatible with the connections between the carriage 130 and a surgical instrument. Further, the carriage 130 is shaped to allow the elongate tube 210 (FIG. 2 of the surgical instrument 120 to pass through an indentation 410 along a side of the carriage. It is difficult to drape the carriage with the plastic sheet due to the shape of the carriage and because it projects from the strut 310.

Figure 5:
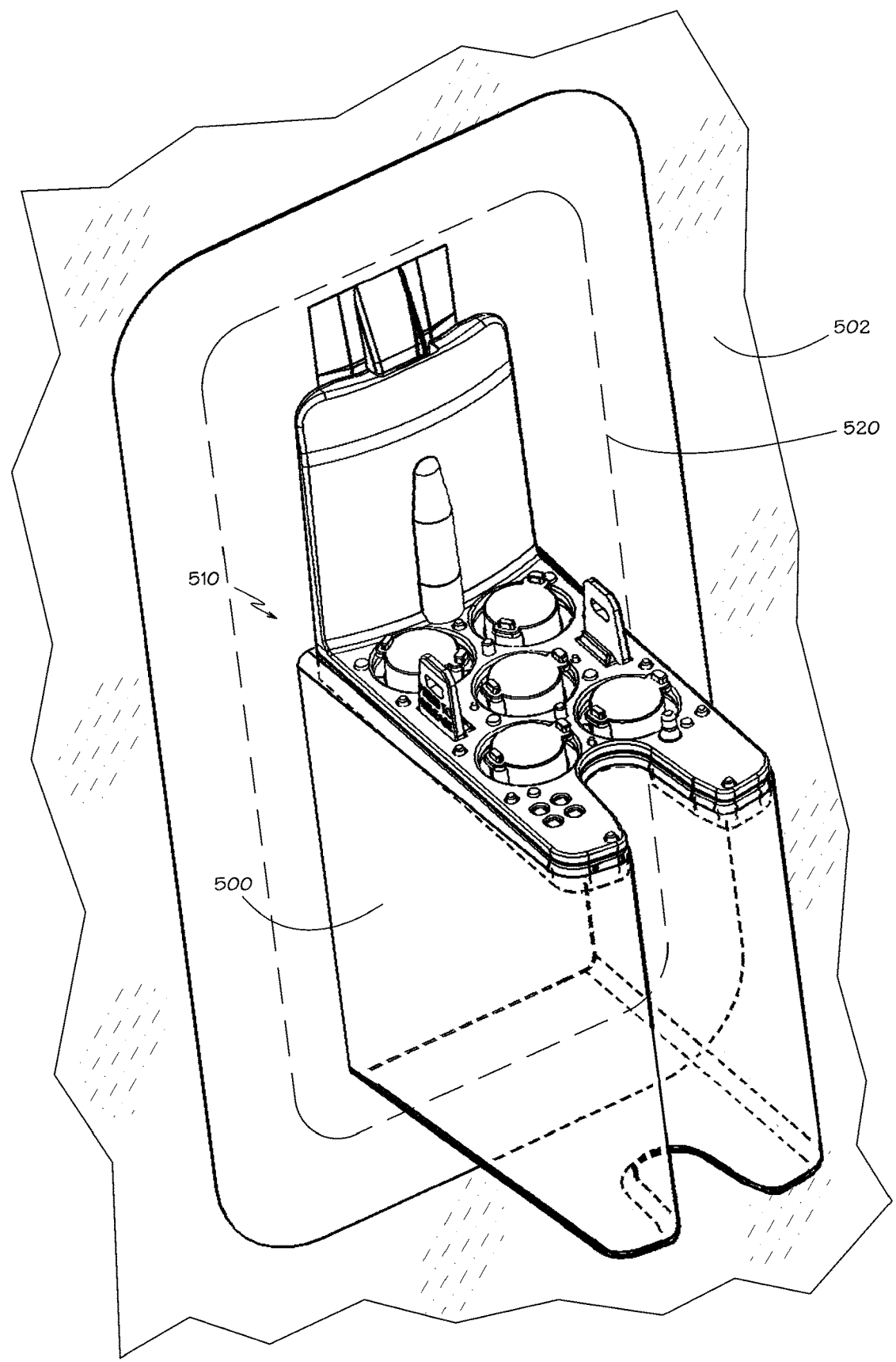
FIG. 5 is a perspective view of a portion of a sterile drape.

FIG. 5 is a perspective view of the portion of the sterile drape that is constructed to be placed around the carriage 130. The sterile drape includes three portions. The first portion is the plastic sheet 300 described above. The second portion is a pouch 500 shaped to fit around the carriage 130. The third portion is a largely rigid instrument sterile adapter (ISA) 510 that engages the control features 400 of the carriage 130 and provides a sterile counterpart of the control features for connection to a surgical instrument. Each of the three portions of the sterile drape overlaps and seals against the adjacent portion so that the three portions form a continuous barrier. The sterile drape is a disposable assembly.

The pouch 500 may be made from a materials such as low density polyethylene (LDPE), ethylene-vinylacetate copolymers (EVA), and/or thermoplastic urethane (TPU), which may be the same material used for the plastic sheet 300 but with a greater thickness. Other suitable materials may be used for the pouch. The pouch 500 may be fabricated from a plastic sheet of an appropriate thickness by a suitable process such as heat-forming, thermo-forming, or vacuum-forming. The pouch 500 may be flexible but it should return to its original shape when not subject to stress. The pouch 500 provides a portion of the drape that is a loose form fit around the carriage 130 to provide a clear work space for the actuators and the surgical instrument. There may be certain areas where the pouch 500 is more closely fitted to the carriage 130, such as the region 410 where a shaft of a surgical instrument passes the carriage. It may be desirable to form the pouch 500 from a transparent or translucent material so that features of the carriage 130, such as indicator lights, can be seen through the pouch. In some embodiments, the pouch may be formed of two or more parts. For example, part of the pouch may be formed from a more rigid material and part of the pouch may be formed from a more flexible material.

An aperture 520 is formed in the plastic sheet 300 where the pouch 500 is joined to the plastic sheet. It is desirable to join the pouch 500 to the plastic sheet 300 with the pouch positioned over the aperture 520 rather than extending through the aperture. The plastic sheet may be joined to the pouch by any process that is compatible with the materials of the sheet and the pouch, such as by heat welding or a pressure sensitive adhesive (PSA). The aperture 520 may be formed in the plastic sheet 300 before or after the pouch 500 is joined to the plastic sheet.

Figure 6:
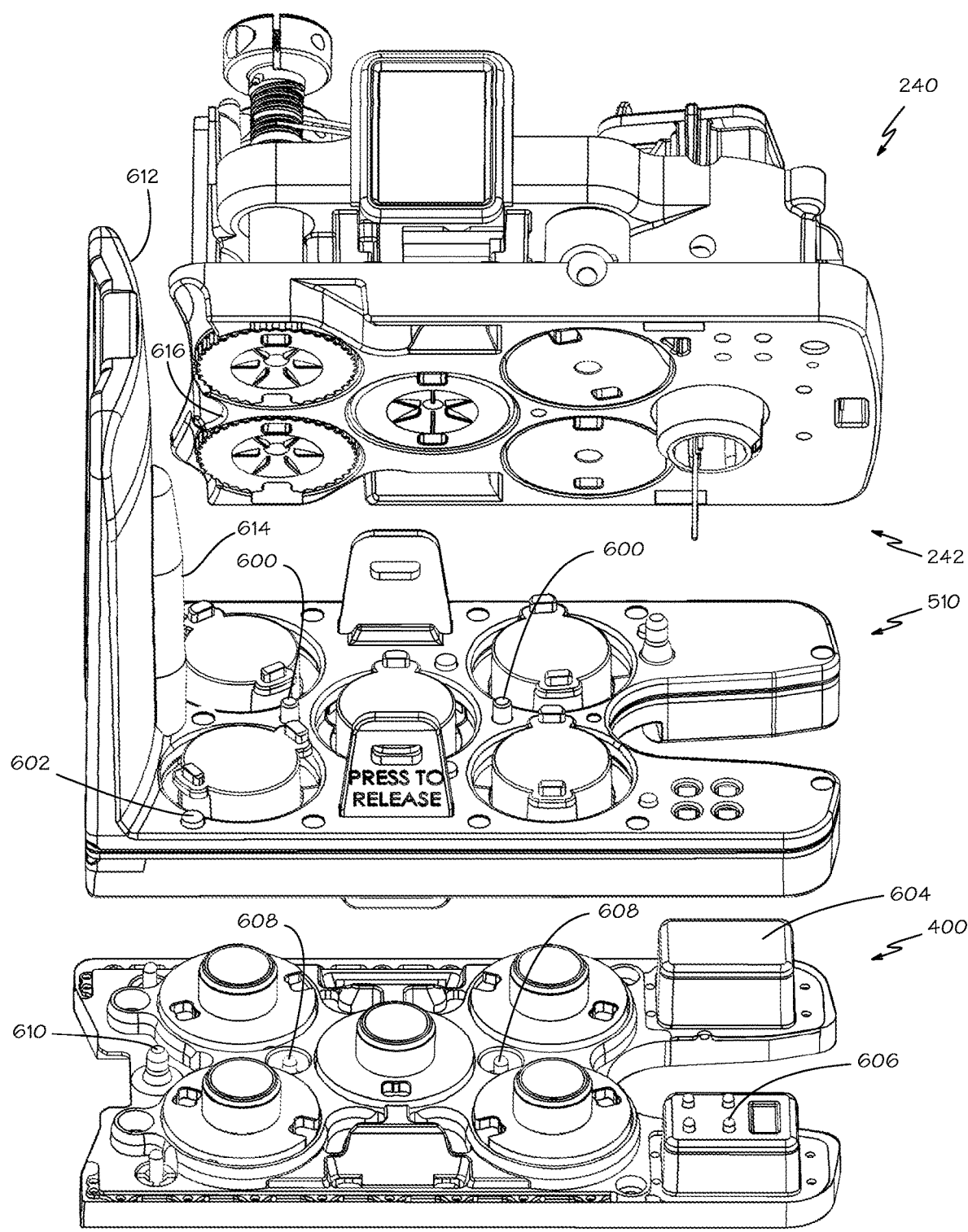
FIG. 6 is a perspective view of a control surface of a carriage, an instrument sterile adapter (ISA), and a surgical instrument.

FIG. 6 is a perspective view of the control surface 400 of the carriage, the ISA 510 (without the pouch or plastic sheet portions of the sterile drape), and a proximal control mechanism 240 of a surgical instrument that has been rotated to show the instrument control surface 242. The ISA 510 is coupled to the control surface 400 of the carriage as suggested by the figure. The ISA 510 provides a control surface that extends all of the control features of the control surface 400 of the carriage as a sterile, disposable surface that can receive the proximal control mechanism 240 of the teleoperated surgical instrument and engage the control features of the instrument control surface 242.

Figure 7:
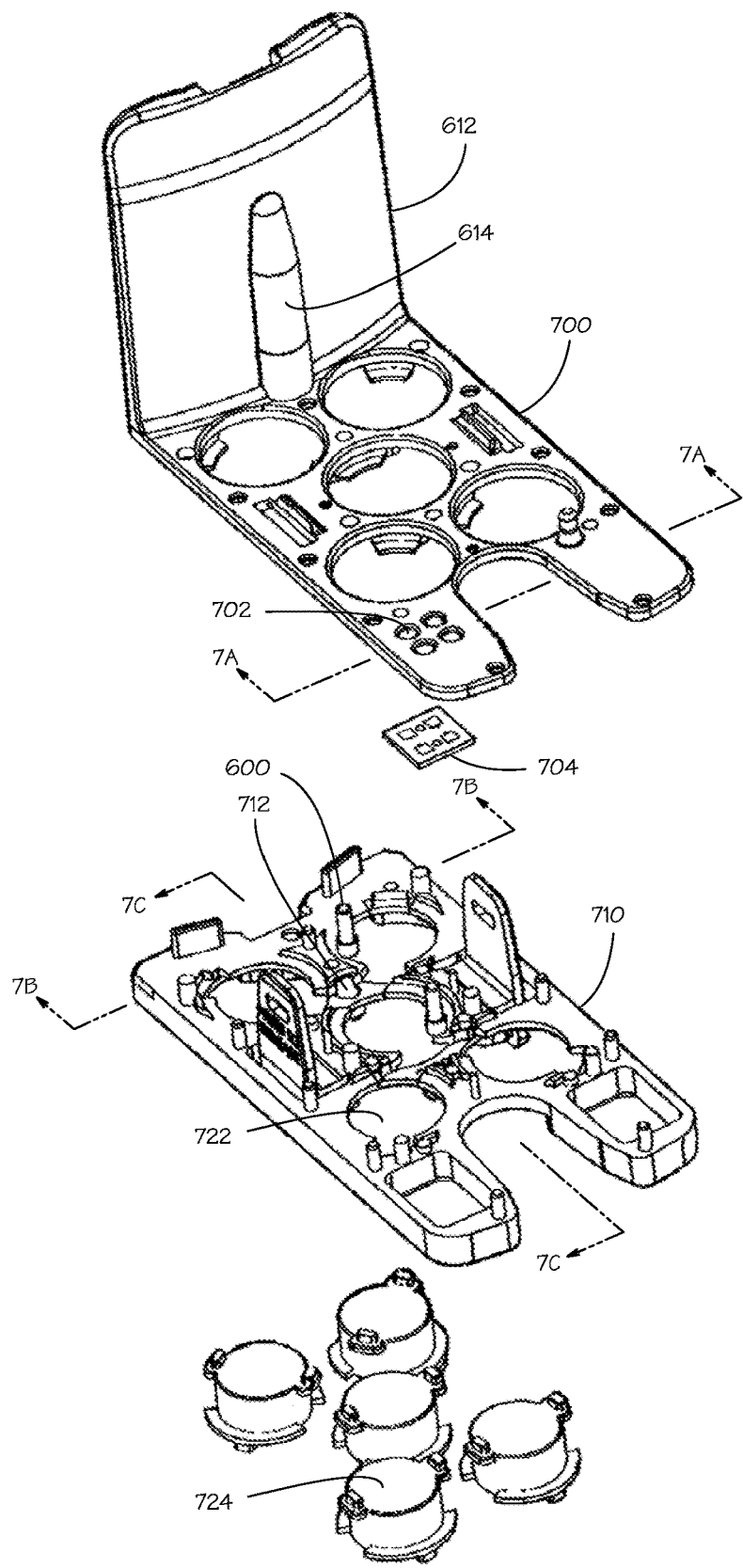
FIG. 7 is an exploded perspective view of the ISA.

FIG. 7 is an exploded perspective view of the ISA 510. The ISA is assembled by inserting coupler disks 724 into openings 722 in a bottom plate 710 of the ISA. The coupler disks 724 may be retained in the openings by that passing tabs on the disks through keyways in the bottom plate and then turning the disks to misalign the tabs and keyways. Presence pins 600 may be inserted into pockets 712 in the bottom plate 710 of the ISA. Flux couplers 704 may be coupled over openings 702 in a top plate 700 of the ISA.

Figure 8:
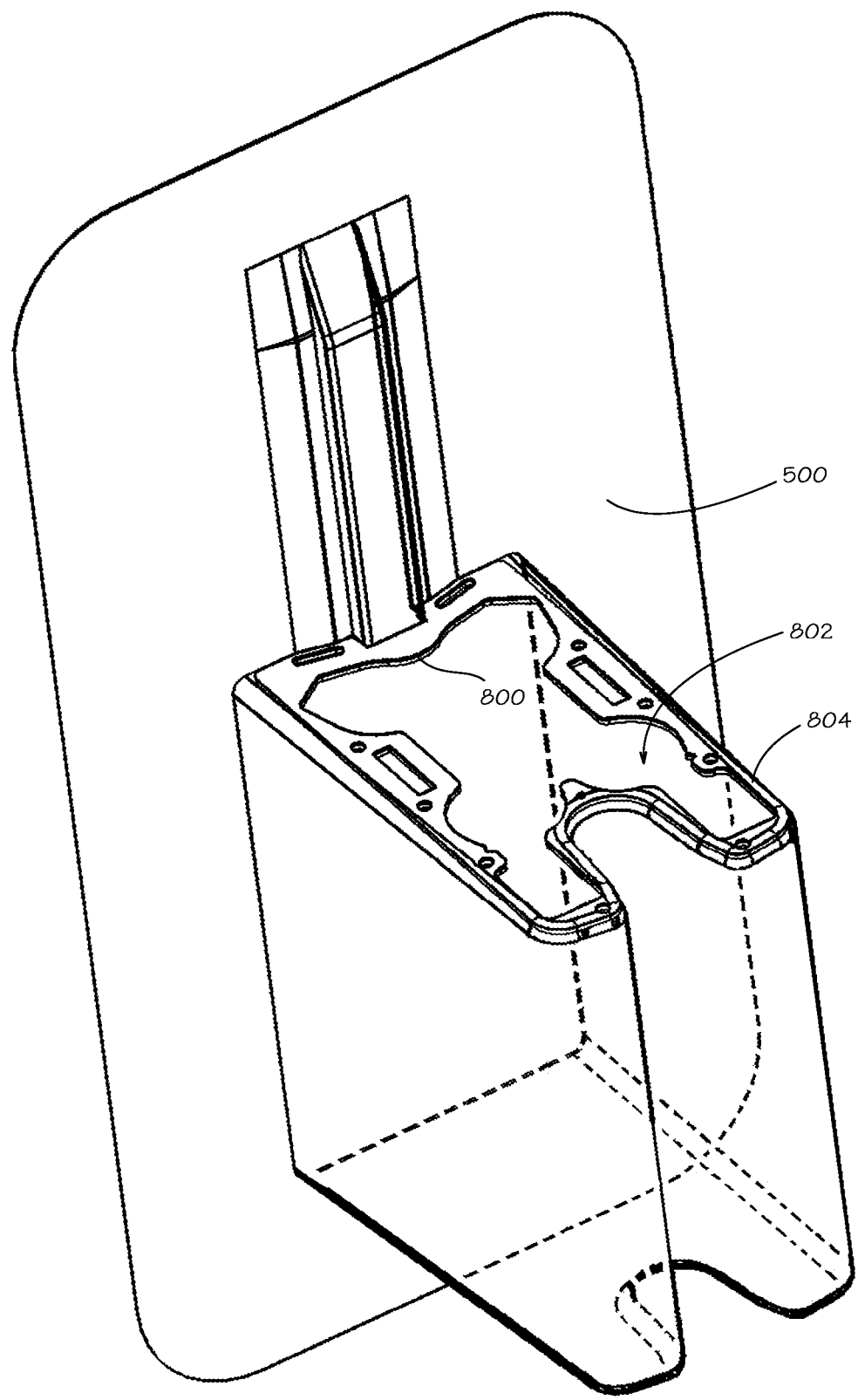
FIG. 8 is a perspective view of a pouch portion of an ISA.

FIG. 8 is a perspective view of the pouch 500. The pouch provides an opening 802 through which the control features—such as the coupler disks 724, the presence pins 600, and the flux coupler 704—communicate between the bottom plate 710 and the top plate 700. The assembled bottom plate 710 is placed on a first side of the pouch 500, i.e. the side of the pouch facing the interior of the pouch cavity, adjacent the opening 802. The assembled top plate 700 is placed on an opposing second side of the pouch, i.e. the side of the pouch facing away from the interior of the pouch cavity, adjacent the opening 802. The pouch 500 is captured between the top plate 700 and the bottom plate 710, which may be joined together by various methods. One method of joining the top plate 700 and the bottom plate 710 is passing pins between the top and bottom plates and through the pouch and heat staking the pins to form a permanent assembly. Other suitable methods of joining the top and bottom plates include ultrasonic welding, pressure sensitive adhesives (PSA), liquid adhesives, and snap fits.

Referring again to FIGS. 6 and 7, the top plate 700 may include a vertical wall portion 612 that is substantially perpendicular to the control surface of the carriage and substantially parallel to the strut 310 (FIG. 4) that supports the carriage 130. The vertical wall portion 612 of the ISA may provide a rigid surface that assists in guiding a surgical instrument into engagement with the ISA and protects the soft surfaces of the sterile drape during that procedure. The vertical wall portion 612 may include a rib 614 that engages a corresponding recess 616 in a proximal control mechanism 240 of a surgical instrument. The rib 614 may be tapered to provide a tolerant initial engagement with the proximal control mechanism 240 that then guides the instrument to a more precise location as the instrument is brought into position to engage the ISA.

Referring again to FIG. 8, some areas 804 that are retained between the bottom plate 710 and the top plate 700 are narrow. If a flexible material is used to form the pouch 500, the material may not be adequately retained between the bottom plate 710 and the top plate 700 because of the pouch material's flexibility and elasticity. A stiffener 800 may be coupled to the pouch 500 to provide a relatively inelastic area that corresponds to the portion of the pouch that is retained between the bottom plate 710 and the top plate 700. The inelastic area may be formed by co-extruding a sheet having a layer of polyethylene terephthalate glycol-modified (PETG) and a layer of thermoplastic urethane (TPU). The stiffener 800 may be cut for the co-extruded sheet. The stiffener 800 may be coupled to the pouch 500 by heat welding the TPU surface to the pouch, which may also be formed from TPU. Other assemblies that provide a flexible pouch 500 with an inelastic area 800 that is retained between the bottom plate 710 and the top plate 700 of the ISA may also be used. Other embodiments may use a pressure sensitive adhesive (PSA) or a liquid adhesive to bond the pouch 500 to one or both of the bottom plate 710 and the top plate 700 to retain the pouch between the plates.

Figure 9:
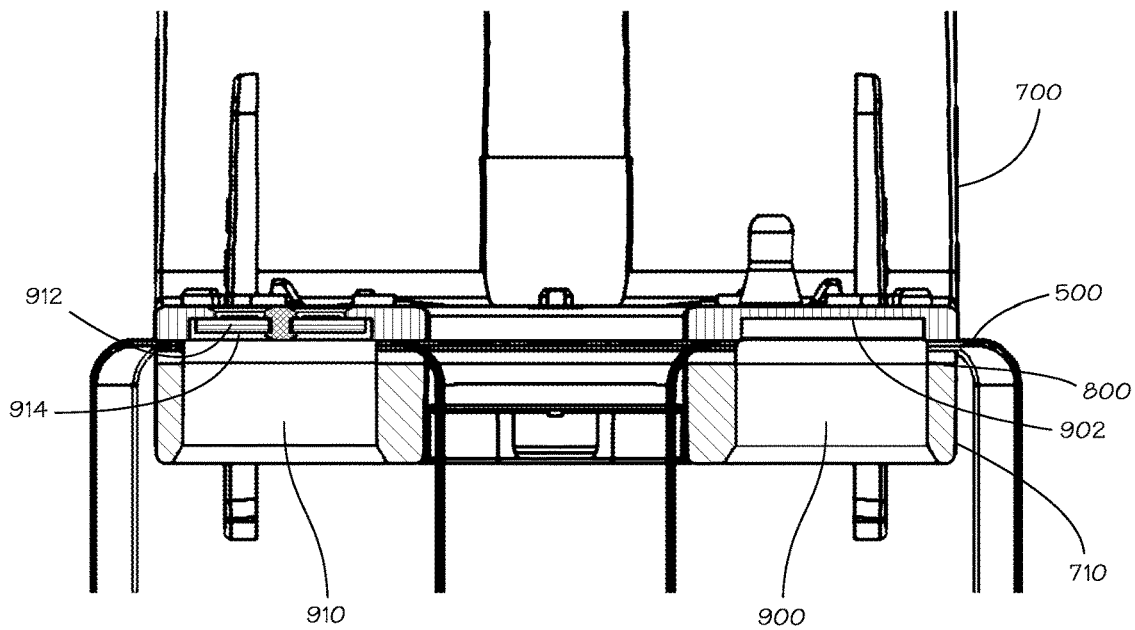
FIG. 9 is a section view of the ISA taken along line 7A-7A in FIG. 7.

FIG. 9 is a section view of the ISA 510 taken along line 7A-7A in FIG. 7. Referring to FIG. 6, the carriage may provide a sensor 604 for reading a radio frequency identification (RFID) device contained in a surgical instrument. The RFID device may require that the sensor 604 be very close to the RFID device because of the presence of metal components nearby. The bottom plate 710 of the ISA may provide a passage 900 that allows the sensor 604 to pass through the bottom plate, the stiffener 800, and the pouch 500 to place an upper surface of the sensor adjacent the top plate 700 of the ISA. Further, a signal transmission area 902 of the top plate 700 that will be adjacent the sensor 604 may be thinned to allow the sensor to be still closer to the RFID device in a surgical instrument.

Referring again to FIG. 6, the carriage may provide a flux connection 606 that provides a connection for electrical and/or optical signals. In the embodiment illustrated, pogo pins 606, spring loaded conductive pins, provide electrical signals to be connected to the surgical instrument. The bottom plate 710 of the ISA may provide a passage 910 that allows the flux connection 606 to pass through the bottom plate, the stiffener 800, and the pouch 500 to be place an upper surface of the flux connection adjacent the top plate 700 of the ISA. The signal transmission area of the top plate 700 that will be adjacent the flux connection may provide openings 912 for a flux connector 904 that closes the openings in the top plate to provide a continuous barrier while providing a path for the electrical and/or optical signals between the flux connection and the surgical instrument.

Figure 10:
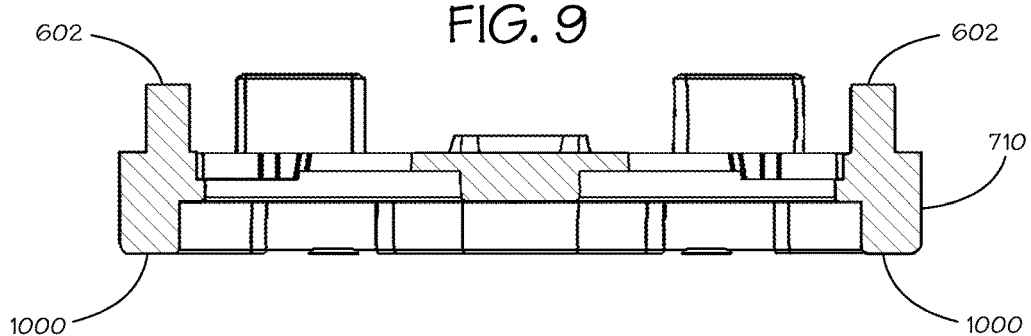
FIG. 10 is a section view of a bottom plate of the ISA taken along line 7B-7B in FIG. 7.

FIG. 10 is a section view of the bottom plate 710 of the ISA taken along line 7B-7B in FIG. 7. It is desirable to position the surgical instrument at a known distance from the control surface 400 of the carriage 130 (FIG. 4). If the surgical instrument is located with respect to the top plate 700 of the ISA, the dimensional tolerances of the bottom plate 710, the stiffener 800, the pouch 500, and the top plate all will affect the position of the surgical instrument, which may not provide the desired precision of location. The bottom plate 710 may include landing pads 602 that provide the datum plane for the surgical instrument. The landing pads 602 extend from the bottom plate 710 through the stiffener 800, the pouch 500, and the top plate 700. The bottom plate 710 may further include mounting surfaces 1000 that provide the datum plane for the mounting of the ISA on the control surface 400 of the carriage 130. Since the landing pads 602 and the mounting surfaces 1000 are opposing parallel surfaces on the solid bottom plate 710, the distance between the landing pads and the mounting surfaces can be controlled with considerable precision. Thus the ISA can position the surgical instrument at a known distance from the control surface 400 of the carriage 130 with precision.

Figure 11:
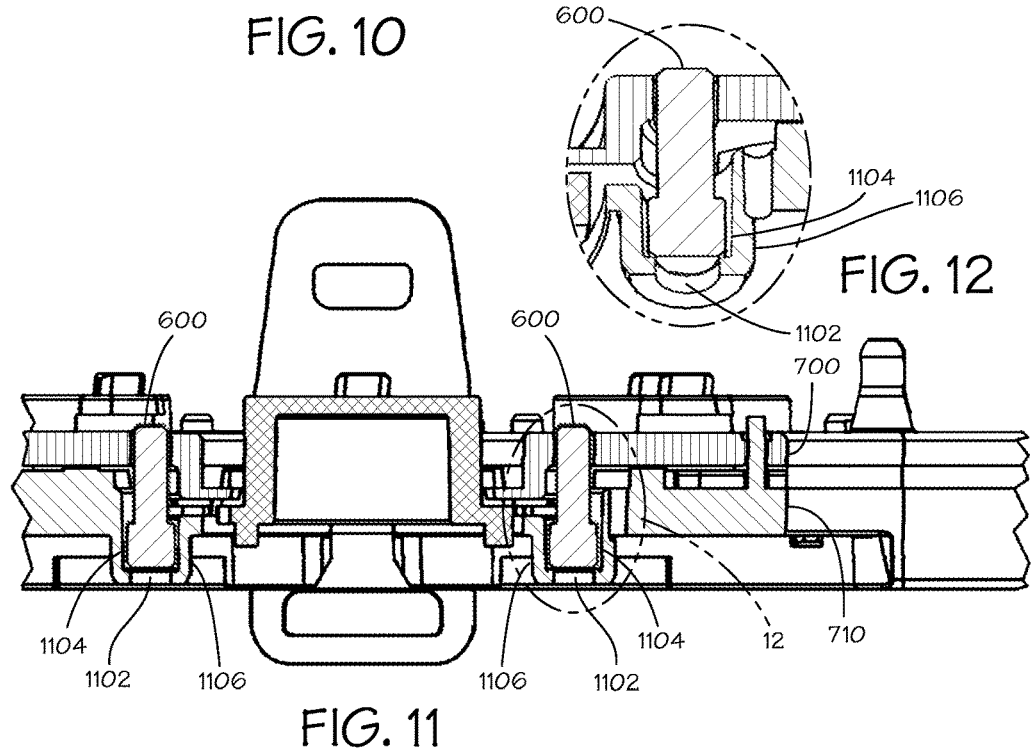
FIG. 11 is a section view of a portion of the ISA and presence pins taken along line 7C-7C in FIG. 7.

FIG. 11 is a section view of a portion of the top 700 and bottom 710 plates of the ISA and presence pins 600 taken along line 7C-7C in FIG. 7. The control system may require a signal that indicates when a surgical instrument has been coupled to the ISA 510. The carriage may provide spring loaded plungers 608 (FIG. 6) that can be depressed to provide a signal to the control system. The bottom plate 710 of the ISA may provide pockets 1104 to receive presence pins 600. Openings 1102 are provided in the bottom plate 710 so that the spring loaded plungers 608 can pass into the pockets 1104 in the bottom plate and lift the presence pins 600 through openings in the top plate 710. The presence pins 600 allow a surgical instrument to depress the spring loaded plungers 608 in the carriage while maintaining a sterile barrier between the surgical instrument and the carriage. When a surgical instrument is coupled to the ISA the presence pins 600 are depressed, perhaps to the position illustrated in FIG. 11, and the spring loaded plungers 608 are likewise depressed to provide a signal to the control system indicating that a surgical instrument is coupled to the ISA.

Figure 12:
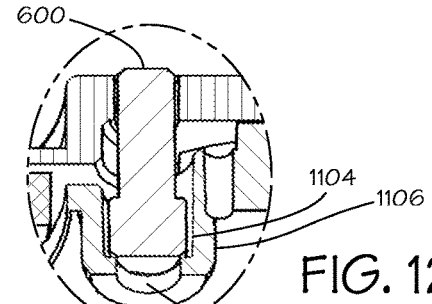
FIG. 12 is a perspective view of a portion of the ISA and a presence pin circled in FIG. 11.

FIG. 12 is a perspective view of a portion of the ISA and a presence pin circled 12 in FIG. 11. As best seen in FIG. 12, the pockets 1104 in the bottom plate 710 may project from the lower surface 1000 of the bottom plate. The protrusions 1106 that house the pockets may extend into the carriage is spaces around the spring loaded plungers 608. This allows the spring loaded plungers to be located below the surface of the carriage that receives the ISA to protect the spring loaded plungers from lateral forces that might damage the plungers.

The protrusions 1106 may be chamfered at the end that enters the carriage to assist in positioning the ISA on the carriage. Referring to FIG. 6, the guide pin 610 on the control surface 400 of the carriage may engage a receptacle on the ISA to laterally position that end of the ISA as it is positioned on the carriage. The protrusions 1106, particularly the protrusion furthest from the vertical wall portion 708 may cooperate with the guide pin 610 engagement to laterally position the opposite end of the ISA and align it for engagement with the control surface 400 of the carriage.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A method for assembling an instrument sterile drape, the method comprising:
   providing a plastic sheet;
   joining a bottom plate located on a first side of the plastic sheet to a top plate located on an opposite second side of the plastic sheet and capturing the plastic sheet between the top plate and the bottom plate as part of an instrument sterile adapter (ISA);
   providing a passage in the bottom plate that allows a flux connection of an instrument carriage to pass through the plastic sheet and the bottom plate to place the flux connection adjacent to the top plate; and
   providing a signal transmission area in the top plate that will be adjacent to an upper surface of the flux connection of the instrument carriage.

2. The method of claim 1 further comprising:
   creating a first opening in the plastic sheet;
   forming a pouch that is thicker than the plastic sheet to fit around the instrument carriage;
   sealing the pouch to the first opening in the plastic sheet;
   creating a second opening in the pouch;
   joining the bottom plate to the top plate at the second opening in the pouch; and
   providing a second passage in the pouch that allows the flux connection of the instrument carriage to pass through the pouch.

3. The method of claim 2 further comprising:
   placing the bottom plate over the second opening on a first side of the pouch;
   placing the top plate over the second opening on a second side of the pouch opposite the first side; and
   joining the bottom plate and the top plate to retain a portion of the pouch between the bottom plate and the top plate.

4. The method of claim 3 further comprising:
   passing pins between the top and bottom plates and through the pouch; and
   heat staking the pins to form a permanent assembly.

5. The method of claim 1 further comprising:
   creating an opening in the signal transmission area of the top plate; and
   closing the opening in the signal transmission area with a flux connector that provides a path for an electrical signal.

6. The method of claim 1 further comprising:
   creating an opening in the signal transmission area of the top plate; and
   closing the opening in the signal transmission area with a flux connector that provides a path for an optical signal.

7. The method of claim 1 further comprising:
   thinning the signal transmission area of the top plate to allow an RFID sensor flux connection to be closer to an RFID device in a surgical instrument attached to the instrument sterile adapter.

8. An instrument sterile drape comprising:
   a plastic sheet;
   a bottom plate located on a first side of the plastic sheet;
   a top plate located on an opposite second side of the plastic sheet;
   means for capturing the plastic sheet between the top plate and the bottom plate as part of an instrument sterile adapter (ISA);

means for allowing a flux connection of an instrument carriage to pass through the plastic sheet and the bottom plate to place the flux connection adjacent to the top plate; and means for transmitting a signal in the top plate that will be adjacent to an upper surface of the flux connection of the instrument carriage.

9. The instrument sterile drape of claim 8 further comprising:

a pouch sealed to a first opening in the plastic sheet, the pouch being thicker than the plastic sheet, the pouch being shaped to fit around the instrument carriage, the pouch including a second opening at which the ISA is coupled with the bottom plate located on a first side of the pouch and the top plate located on an opposing second side of the pouch, and means for allowing the flux connection to pass through the pouch.

10. The instrument sterile drape of claim 9 further comprising:

means for joining the bottom plate and the top plate to retain a portion of the pouch between the bottom plate and the top plate.

11. The instrument sterile drape of claim 10 wherein the means for joining the bottom plate and the top plate further comprises:

pins passing between the top and bottom plates and through the pouch and heat staked to form a permanent assembly.

12. The instrument sterile drape of claim 8 wherein the means for transmitting a signal further comprises:

means for closing an opening in the top plate and providing a path for an electrical signal.

13. The instrument sterile drape of claim 8 wherein the means for transmitting a signal further comprises:

means for closing an opening in the top plate and providing a path for an optical signal.

14. The instrument sterile drape of claim 8 wherein the means for transmitting a signal further comprises:

means for allowing an RFID sensor flux connection to be closer to an RFID device in a surgical instrument attached to the instrument sterile adapter.

15. An instrument sterile drape comprising:

a plastic sheet; and an instrument sterile adapter (ISA) coupled to the plastic sheet, the ISA including a bottom plate located on a first side of the plastic sheet and a top plate located on a second side of the plastic sheet and joined to the bottom plate with the plastic sheet captured between the top plate and the bottom plate to form a permanent assembly, the bottom plate including a passage that allows a flux connection of an instrument carriage to pass through the plastic sheet and the bottom plate to place the flux connection adjacent to the top plate, and the top plate including a signal transmission area that will be adjacent to an upper surface of the flux connection of the instrument carriage when the flux connection is passed through the passage in the bottom plate.

16. The instrument sterile drape of claim 15 further comprising:

a pouch sealed to a first opening in the plastic sheet, the pouch being thicker than the plastic sheet, the pouch being shaped to fit around the instrument carriage, the pouch including a second opening at which the ISA is coupled with the bottom plate located on a first side of the pouch and the top plate located on an opposing second side of the pouch, and the passage allowing the flux connection to pass through the pouch.

17. The instrument sterile drape of claim 16 wherein the top plate is joined to the bottom plate by passing pins between the top and bottom plates and through the pouch and heat staking the pins to form a permanent assembly.

18. The instrument sterile drape of claim 15 further comprising a flux connector that closes an opening in the signal transmission area of the top plate and provides a path for an electrical signal.

19. The instrument sterile drape of claim 15 further comprising a flux connector that closes an opening in the signal transmission area of the top plate and provides a path for an optical signal.

20. The instrument sterile drape of claim 15 wherein the signal transmission area of the top plate is thinned to allow an RFID sensor in the flux connection to be closer to an RFID device in a surgical instrument attached to the instrument sterile adapter.

* * * * *